United States Patent [19]
Rehfinger et al.

[11] Patent Number: 6,075,169
[45] Date of Patent: Jun. 13, 2000

[54] PROCESS FOR PREPARING OXIDATION PRODUCTS FROM CYCLOHEXANE IN COUNTERFLOW

[75] Inventors: Alwin Rehfinger, Mutterstadt; Martin Gann, Freinsheim, both of Germany; Robert Märkl, Randolph, N.J.; Rüdiger Schmitt, Frankenthal, Germany

[73] Assignee: BASF Aktiengesellshcaft, Ludwigshafen, Germany

[21] Appl. No.: 09/284,411

[22] PCT Filed: Oct. 17, 1997

[86] PCT No.: PCT/EP97/05740

§ 371 Date: Apr. 14, 1999

§ 102(e) Date: Apr. 14, 1999

[87] PCT Pub. No.: WO98/17612

PCT Pub. Date: Apr. 30, 1998

[30] Foreign Application Priority Data

Oct. 18, 1996 [DE] Germany .......................... 196 43 154

[51] Int. Cl.$^7$ .................................................. C07C 45/33

[52] U.S. Cl. ........................ 568/358; 568/357; 568/360; 568/376; 568/836

[58] Field of Search ...................... 568/357, 358, 568/360, 376, 836

[56] References Cited

U.S. PATENT DOCUMENTS

| | | | |
|---|---|---|---|
| 3,530,185 | 9/1970 | Pugi | 260/586 |
| 3,957,876 | 5/1976 | Rapoport et al. | 260/586 |
| 3,987,100 | 10/1976 | Barnette et al. | 260/586 |
| 4,587,363 | 5/1986 | Hartig et al. | 568/357 |
| 4,675,450 | 6/1987 | Lyon et al. | 568/360 |

*Primary Examiner*—Gary Geist
*Assistant Examiner*—Sreeni Padmanabhan
*Attorney, Agent, or Firm*—Keil & Weinkauf

[57] ABSTRACT

In a process for preparing oxidation products of cyclohexane by catalytic oxidation with oxygen-containing gases in the liquid phase, where the gases are brought into contact essentially uniformly with the liquid cyclohexane in a reaction zone, liquid cyclohexane and the oxygen-containing gases are passed in countercurrent through the reaction zone.

14 Claims, No Drawings

PROCESS FOR PREPARING OXIDATION PRODUCTS FROM CYCLOHEXANE IN COUNTERFLOW

This is the U.S. National Stage application of PCT/EP97/05740 filed Oct. 17, 1997 now WO98/17612 published Apr. 30, 1998.

The present invention relates to a continuous process for preparing oxidation products of cyclohexane by catalytic oxidation with oxygen-containing gases in the liquid phase, where the gases are brought into contact essentially uniformly with liquid cyclohexane in at least one reaction zone.

Processes for oxidizing hydrocarbons using molecular oxygen and in particular the oxidation of cyclohexane to give cyclohexanol and cyclohexanone are known from the prior art. Thus, DE-A-21 36 744 and U.S. Pat. No. 3,957,876 describe a process for preparing solutions containing cyclohexyl hydroperoxide by zonewise oxidation of cyclohexane, in which process a mixture of cyclohexane and a soluble cobalt catalyst is allowed to flow from the top downward through a tray column and an oxygen-containing gas is allowed to flow in countercurrent from the bottom upward through the column. The column has an oxygen consumption zone at the upper end and adjacent thereto in a downward direction oxidation zones, with the latter each being able to be fed separately with different amounts of oxygen. The process is aimed exclusively at the preparation of cyclohexyl hydroperoxide which is obtained in an amount of 15% by weight, based on the total amount of oxidation products.

U.S. Pat No. 4,675,450 describes a process for preparing cyclohexyl hydroperoxide similar to DE-A-21 36 744, with the cyclohexane oxidation being carried out in the presence of a soluble cobalt catalyst and also a phosphoric ester.

DE-A-12 87 575 describes a process for the oxidation of liquid cyclohexane in a plurality of directly successive oxidation stages, with oxygen-containing gas being introduced into each oxidation stage. This introduction is carried out in such a way that the rate at which oxygen is fed into each stage corresponds essentially to the rate at which oxygen is consumed, with inert gas being additionally introduced into the last oxidation stage. This unavoidably results in a nonuniform oxygen feed rate and oxygen distribution in the reaction mixture, which leads to a reduction in yield. The reaction zone is divided into chambers by metal sheets which are bent downward and do not cover the entire cross section. The gas is fed in below these metal sheets into the descending gas phase of the subsequent oxidation stage, which can, in a reaction procedure for using "flooded trays" which is described as suitable, likewise lead to a nonuniform feeding-in of oxygen, to a nonuniform flow of the reaction mixture and, in the most unfavorable case, to formation of oxygen-containing gas spaces under the trays, which increases the danger of an ignitable mixture being formed and of an explosion.

DE-C-25 15 419, corresponding to U.S. Pat. No. 3,987,100, describes a process for preparing cyclohexanone and cyclohexanol by oxidation of cyclohexane in a tray column operated in countercurrent in the presence of a soluble, binary catalyst system containing from 0.1 to 5 ppm of cobalt and from 0.02 to 0.9 ppm of chromium. In this process, the individual trays are configured, for example, as perforated metal sheets through which the oxygen-containing gas can rise and the descending cyclohexane can flow.

Analogously to DE-A-12 87 575, oxygen-containing gas can be additionally introduced onto some or all of the trays (with the exception of an oxygen consumption zone at the top of the column). This introduction is again carried out in such a way that virtually all the oxygen introduced in each stage is also consumed in that stage. Since, in addition, the number and/or the size of the holes in the perforated metal sheets increases from the bottom to the top of the reactor and since no oxygen is fed into the upper trays, a nonuniform feeding-in of oxygen, a nonuniform oxygen distribution in the reactor and a nonuniform flow of the reaction mixture, as already described above for the case of DE-A-12 87 575, occur in this process. Since, in addition, the free tray area is very low at about 1.2%, the formation of gas spaces under the trays together with the above-described danger of explosion can result in this process too.

None of the abovementioned documents describes a process for preparing oxidation products of cyclohexane in which the oxygen-containing gas is introduced directly into the liquid phase and forms bubbles therein so that there is no longer any continuous gas phase in the reactor and in which the reaction mixture is exposed very uniformly to oxygen.

EP-A-0 135 718 describes a continuous process for the oxidation of hydrocarbons in the liquid phase and specifically for the oxidation of cyclohexane, where an oxygen-containing gas is introduced into the liquid reaction mixture at a plurality of points along a reaction zone by means of downward-directed nozzle orifices. The reaction zone is here divided into a plurality of chambers, with no continuous gas phase being able to be formed.

This is achieved in practice, for example, by means of an upright bubble column divided into chambers by perforated metal sheets and by passing cyclohexane together with a cobalt catalyst dissolved therein through the bubble column from the bottom upward. The oxygen-containing gas is fed in above the perforated metal sheets by means of nozzles, with bubbles of a defined size being formed by means of an exactly defined gas exit velocity and amount. The liquid reaction mixture is thus brought into essentially uniform contact with molecular oxygen over the volume of the reaction zone and the disadvantages of DE-A-12 87 575 are avoided. In this process, the liquid hydrocarbons and the oxygen-containing gases are passed through the reactor in cocurrent. In terms of the high cyclohexane content of the waste gas and the selectivity of the oxidation in respect of the formation of cyclohexanol and cyclohexanone, this process is still in need of improvement. This applies particularly to a reduction in the amounts of the acid-containing by-products (e.g. caproic acid) which have to be removed from the reaction mixture by costly washing with water and sodium hydroxide solution, giving wastewater having a high salt loading and an increased TOC (total organic carbon) content.

It is an object of the present invention to provide an improved process for preparing oxidation products of cyclohexane, with the above-described disadvantages being avoided.

We have found that this object is achieved by a process for preparing oxidation products of cyclohexane by oxidation with oxygen-containing gases in the liquid phase if liquid cyclohexane and the oxygen-containing gases are passed in countercurrent through a reaction zone and a uniform exposure of the reaction medium to oxygen is ensured.

The present invention accordingly provides a process for preparing oxidation products of cyclohexane by catalytic oxidation with oxygen-containing gases in the liquid phase, where the gases are brought into contact essentially uniformly with the liquid cyclohexane in at least one reaction zone, wherein liquid cyclohexane and the oxygen-containing gases are passed in countercurrent through the reaction zone.

Suitable reactors for the process of the present invention are reaction vessels having horizontal or preferably upright reaction zones. According to a preferred embodiment, these reaction zones are divided into chambers or sections in order to prevent admixing. In the case of horizontal reaction zones this can be achieved, for example, by means of overflows or dividing walls having openings; in the case of upright reaction zones this can be effected, for example, by means of perforated metal sheets installed at regular intervals.

Advantageously, these measures result in a continuous gas phase no longer being formed in the reaction zone.

In the process of the present invention, in contrast to EP-A-0 135 718, the liquid cyclohexane and the oxygen-containing gases are passed in countercurrent through the reaction zone.

The oxidation is carried out using oxygen-containing gases in which molecular oxygen is present. The oxygen concentration is preferably in a range from 5 to 30% by volume. The oxygen-containing gases are preferably introduced into the liquid cyclohexane at a plurality of points along the reaction zone by means of nozzles. The nozzle orifices advantageously point downward.

According to a preferred embodiment of the process of the present invention, the exit velocity of the oxygen-containing gases at each nozzle orifice is from 0.01 to 1 m/s, preferably from 0.03 to 0.3 m/s.

Furthermore, the amount of oxygen-containing gases coming out of each nozzle orifice is preferably from 0.01 to 10 l/s, preferably from 0.1 to 1.0 l/s.

The nozzle orifices are distributed essentially uniformly over the volume of the reaction zone. This is achieved, for example, by arranging nozzle orifices at a plurality of points at essentially equal intervals along the reaction zone, with these nozzle openings being distributed uniformly over the cross section of the reaction zone.

The spacings along the reaction zone preferably correspond to from 0.1 to 3 times the diameter of the reaction zone and are, in particular, selected such that the molecular oxygen in the rising gas bubbles from the previous feed point has not yet been completely consumed but is, for example, from 60 to 90% of the original content. As a result of this process measure, the cyclohexane to be oxidized is exposed spatially essentially uniformly to the oxygen-containing gas. Essentially the same amount of gas is fed in through each nozzle orifice. Combination of the two measures just described, namely feeding in essentially equal amounts of gas and carrying this out at points along the reaction zone at which the oxygen from a previous feed point has not yet reacted completely, leads to a uniform oxygen concentration in the reactor. This distinguishes the process of the present invention from processes described in DE-A-12 87 575 and similar processes.

Feeding the oxygen-containing gas into the liquid cyclohexane phase via nozzle orifices, as described above, produces bubbles having a defined diameter, preferably $\geq 10$ mm, for example from 10 to 100 mm. These bubbles first have a larger diameter than the equilibrium bubbles into which they disintegrate along the reaction zone. In the present context, equilibrium bubbles are bubbles which form at a certain distance from the nozzle orifice as a result of division or coalescence processes. For the example of the cyclohexane/air system, equilibrium bubbles having a mean diameter of from about 1 to 10 mm result.

In a suitable embodiment of an apparatus for feeding in the oxygen-containing gas, each gas exit point can be supplied uniformly with the oxygen-containing gas, for example via feed lines having a large number of very small drilled holes which effect a defined pressure drop. From each drilled hole, the gas goes into a space which is closed at the top and open in a downward direction and has dimensions such that the above-described preferred gas exit amounts and velocities into the liquid reaction medium are achieved. For this purpose, it is possible, for example, to introduce the oxygen-containing gases through a narrow drilled hole into a widened section which is open in a downward direction and, with the exception of the narrow drilled hole, is closed at the top. The configuration of this widened section can be cylindrical, conical, rectangular, square, trumpet-shaped or bell-shaped, with the bottom edge of the widened section being able to be serrated or oblique if desired. The geometric dimensions of this widened section depend on the above-described gas-exit velocities and gas exit amounts at the nozzle orifice and can easily be calculated by a person skilled in the art using the data indicated.

A soluble catalyst, preferably based on cobalt, is added to the cyclohexane to be oxidized. Suitable catalysts are described, for example, in DE-C-25 15 419.

The reaction temperature in the reaction zone is from 120 to 180° C., preferably from 130 to 160° C., and the reaction pressure is from 5 to 30 bar, preferably from 10 to 20 bar. Pressure and temperature are matched to one another so that the reaction occurs in the liquid phase at every point in time.

According to a specific embodiment of the process of the present invention for preparing oxidation products of cyclohexane, an upright reaction zone is used. The reaction can be carried out, for example, in one or more tower reactors connected in series. The upright reaction zone is divided into chambers by means of perforated metal sheets which are arranged at uniform intervals. These perforated metal sheets advantageously have a free cross section (total area of the holes) of from 3 to 20%, in particular from 5 to 10%. Above each perforated metal sheet, nozzles whose orifices preferably point downward are distributed uniformly over the cross section, with the feed orifices being able to be provided with widened sections. Liquid cyclohexane is passed through this reaction zone from the top downward. At the same time, an oxygen-containing gas is fed in through the nozzles. Liquid cyclohexane and the oxygen-containing gases are passed in countercurrent through the reaction zone and the waste gas from the reaction is separated off at the top of the reaction zone. The reaction is carried out, for example, at from about 140 to 160° C. and a pressure of from about 12 to 16 bar.

The ratios of molecular oxygen-containing gases fed in and cyclohexane are preferably matched to one another so that the waste gas leaving the reaction zone has a molecular oxygen content of not more than 2.5% by volume, eg. from 0.1 to 1.5% by volume.

Furthermore, the waste gas separated off at the top still has a cyclohexane content of at most 45% by volume, preferably at most 40% by volume, and this cyclohexane can be returned to the reactor after condensation. In this way, the process of the present invention advantageously makes it possible to lower the cyclohexane content of the waste gas which, in the case of the waste gas-limited reactors used, allows an increase in the capacity, ie. the maximum cyclohexane conversion able to be achieved. The temperature of the waste gas is preferably lower than the lowest reaction temperature in the reaction zone.

The crude oxidation mixture is worked up by the customary methods. These include, for example, scrubbing with water and/or aqueous alkali such as NaOH, with acid-containing and/or salt-containing wastewater being formed. The separation of the purified oxidation mixture into the main products cyclohexanol and cyclohexanone and also the removal of unreacted cyclohexane and of further oxidation products formed in subordinate amounts is carried out in a customary manner, eg. by fractional distillation.

The process of the present invention advantageously makes possible a uniform distribution of the molecular oxygen in the cyclohexane to be oxidized, without needing any further mechanical means for mixing. In particular, no continuous gas phase is formed.

Conveying the reactants in countercurrent through the reaction zone enables the above-described disadvantages to be avoided. In this way, the total conversion of the cyclohexane is increased and at the same time the selectivity of the oxidation in respect of a preferential formation of cyclohexanol and cyclohexanone is improved. In particular, a reduction in the amount of carboxylic acids (caproic acid) in the oxidation products results in a lower acid or salt loading of the wastewater which is obtained on scrubbing the crude oxidation mixture with water and aqueous alkali.

The process is illustrated by the following non-limiting examples.

EXAMPLES

Example 1 (Comparison)

Cyclohexane is oxidized in an oxidation system comprising three reactors connected in series (volume of each: 40 m$^3$, height: 16 m, diameter: 1.8 m), a work-up section (removal of the acids by means of water scrub and also extraction and neutralization with sodium hydroxide solution) and a distillation section. The reactors are provided with a gas distributor which distributes the air uniformly over the reactor cross section and the reactor height. The liquid contents are treated with gas at 7 levels at intervals of 2 m. To reduce admixing, perforated metal sheets, (holes diameter: 40 mm, free area based on the reactor cross section: 4%) are installed in the reactor 30 cm below each gas distributor. The gas distributor of each level is configured such that the air exits at the underside of the gas-introduction tubes (NW 32) through 33 drilled holes (Ø 3 mm), which are distributed uniformly over the reactor cross section. Each drilled hole is provided with a sheathing tube (L: 60 mm, Ø: 25 mm). The gas exit velocity under operating conditions is 0.25 m/s. The reactor system (pressure at the top: about 13 bar) is fed from below with 80 metric t/h of cyclohexane at 140° C. and is operated in cocurrent. Before entry into the first reactor, the cyclohexane is admixed with 0.1 ppm of Co in the form of the ethylhexenoic salt.

Example 2 (according to the present invention)

The oxidation system is operated in a similar way to Example 1, but in countercurrent with the cyclohexane being added from the top.

The results of the experiments are summarized in Table 1.

TABLE 1

| | Example 1 (Cocurrent) | Example 2 (Countercurrent) |
|---|---|---|
| Maximum cyclohexane conversion [%] (limited on the waste gas side) | 4.9 | 5.6 |
| Cyclohexane conversion [%] | 4.9 | 5.0 |
| Selectivity in respect of cyclohexanol/cyclohexanone [%] | 77.5 | 78.3 |

TABLE 1-continued

| | Example 1 (Cocurrent) | Example 2 (Countercurrent) |
|---|---|---|
| Waste gas temperature [° C.] | 153 | 141 |

As Table 1 shows, the cyclohexane oxidation is significantly improved by the countercurrent process, with reserves in respect of a further capacity increase (maximum cyclohexane conversion limited on the waste gas side) still being available.

We claim:

1. A process for preparing oxidation products of cyclohexane by catalytic oxidation with oxygen-containing gases in the liquid phase at elevated temperature, where the gases are brought into contact essentially uniformly with the liquid cyclohexane in at least one upright reaction zone, wherein liquid cyclohexane and the oxygen-containing gases are passed in countercurrent through the reaction zone wherein the liquid cyclohexane is passed through the reaction zone from the top downward, the oxygen containing gasses are introduced through a plurality of nozzles, the waste gas from the reaction is separated off at the top of the reaction zone and the reaction zone is divided into a plurality of chambers by means of perforated metal sheets so that no continuous gas phase is formed in the reaction zone.

2. A process as claimed in claim 1, wherein the temperature of the waste gas is lower than the lowest reaction temperature in the reaction zone.

3. A process as claimed in claim 1, wherein the exit velocity of the oxygen-containing gases at each nozzle orifice is from 0.01 to 1 m/s and the amount coming out of each nozzle orifice is from 0.001 to 10 l/s.

4. A process as claimed in claim 1, wherein the exit velocity of the oxygen-containing gases at each nozzle orifice is from 0.03 to 0.3 m/s and the amount coming out of each nozzle orifice is from 0.1 to 1.0 l/s.

5. A process as claimed in claim 1, wherein the oxygen-containing gases are fed in at intervals along the reaction zone which correspond to from 0.1 to 3 times the diameter of the reaction zone, with the nozzle orifices which feed in the gases being distributed uniformly over the cross section of the reaction zone.

6. A process as claimed in claims 1, wherein the reaction zone is divided into a plurality of chambers which are connected to one another.

7. A process as claimed in claim 1, wherein the oxygen-containing gas is fed into the reaction zone at points at which the oxygen from a previous feed point has not yet reacted completely.

8. A process as claimed in claim 1, wherein the reaction temperature is from 120 to 180° C.

9. A process as claimed in claim 1, wherein the reaction temperature is from 130 to 160° C.

10. A process as claimed in claim 1, wherein the reaction pressure is from 5 to 30 bar.

11. A process as claimed in claim 1, wherein the reaction pressure is from 10 to 20 bar.

12. A process as claimed in claim 1, wherein the oxygen concentration of the oxygen-containing gases is from 5 to 30% by volume.

13. A process as claimed in claim 1, wherein the waste gas contains most 45% by volume of cyclohexane.

14. A process as claimed in claim 1, wherein the waste gas contains most 40% by volume of cyclohexane.

* * * * *

UNITED STATES PATENT AND TRADEMARK OFFICE
CERTIFICATE OF CORRECTION

PATENT NO. : 6,075,169
DATED : June 13, 2000
INVENTOR(S) : Rehfinger et al.

Page 1 of 1

It is certified that error appears in the above-identified patent and that said Letters Patent is hereby corrected as shown below:

<u>Column 6,</u>
Line 63, "contains most" should be -- contains at most --.
Line 65, "comtains most" should be -- contains at most --.

Signed and Sealed this

Fourteenth Day of August, 2001

*Attest:*

*Attesting Officer*

NICHOLAS P. GODICI
*Acting Director of the United States Patent and Trademark Office*